(12) United States Patent
Wentorf et al.

(10) Patent No.: US 10,172,677 B2
(45) Date of Patent: Jan. 8, 2019

(54) SYSTEM AND METHOD TO LOCATE SOFT TISSUE FOR PREOPERATIVE PLANNING

(71) Applicant: Zimmer, Inc., Warsaw, IN (US)

(72) Inventors: Fred A. Wentorf, Warsaw, IN (US); Nolan C. Jones, Warsaw, IN (US); Shanon N. Roberts, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 29 days.

(21) Appl. No.: 15/214,071

(22) Filed: Jul. 19, 2016

(65) Prior Publication Data

US 2017/0020609 A1    Jan. 26, 2017

Related U.S. Application Data

(60) Provisional application No. 62/196,496, filed on Jul. 24, 2015.

(51) Int. Cl.
*G06K 9/00* (2006.01)
*A61B 34/10* (2016.01)
(Continued)

(52) U.S. Cl.
CPC .............. *A61B 34/10* (2016.02); *A61B 5/055* (2013.01); *A61B 6/03* (2013.01); *A61B 6/461* (2013.01);
(Continued)

(58) Field of Classification Search
CPC .......... A61B 17/1764; A61B 2034/105; A61B 2034/108; A61B 34/10; A61B 5/055;
(Continued)

(56) References Cited

U.S. PATENT DOCUMENTS

| 8,884,618 B2 | 11/2014 | Mahfouz |
| 8,989,460 B2 * | 3/2015 | Mahfouz ............... A61F 2/3094 382/128 |

(Continued)

FOREIGN PATENT DOCUMENTS

| CN | 107847275 A | 3/2018 |
| WO | WO-2013177334 A1 | 11/2013 |

(Continued)

OTHER PUBLICATIONS

"International Application Serial No. PCT/US2016/042943, International Search Report dated Oct. 5, 2016", 4 pgs.

(Continued)

*Primary Examiner* — Tom Y Lu

(74) *Attorney, Agent, or Firm* — Schwegman Lundberg & Woessner, P.A.

(57) ABSTRACT

Methods and systems for determining a patient specific soft tissue location within a joint are discussed. For example, a method can include imaging a target location for an orthopedic implant to collect image data regarding a morphology of the patient, the morphology including at least one of bone size and bone feature. The method can additionally include accessing stored soft tissue data and bone data corresponding to the target location of the orthopedic implant, locating a soft tissue of the patient based at least in part upon the soft tissue data and bone data and the image data, and displaying data including the location of the soft tissue of the patient. This data can be used to created patient specific surgical jigs according to one example of the present application.

15 Claims, 7 Drawing Sheets

(51) Int. Cl.
*A61F 2/38* (2006.01)
*A61B 5/055* (2006.01)
*A61B 6/03* (2006.01)
*A61B 6/00* (2006.01)
*A61B 17/17* (2006.01)
*G06T 7/00* (2017.01)
*A61B 34/00* (2016.01)

(52) U.S. Cl.
CPC .............. *A61B 6/487* (2013.01); *A61B 6/505* (2013.01); *A61B 6/5217* (2013.01); *A61B 17/1764* (2013.01); *A61F 2/38* (2013.01); *G06T 7/0012* (2013.01); *A61B 2034/105* (2016.02); *A61B 2034/108* (2016.02); *A61B 2034/256* (2016.02); *G06T 2207/30008* (2013.01)

(58) Field of Classification Search
CPC ........... A61B 6/03; A61B 6/461; A61B 6/487; A61B 6/505; A61B 6/5217; A61B 2034/256; A61F 2/38; G06T 2207/30008; G06T 7/0012
See application file for complete search history.

(56) References Cited

U.S. PATENT DOCUMENTS

| | | | |
|---|---|---|---|
| 9,226,796 B2 * | 1/2016 | Bowling | A61B 34/32 |
| 9,820,818 B2 * | 11/2017 | Malackowski | A61B 34/32 |
| 9,987,092 B2 * | 6/2018 | Hladio | A61B 17/1746 |
| 2013/0211531 A1 | 8/2013 | Steines et al. | |
| 2013/0317510 A1 | 11/2013 | Couture et al. | |
| 2015/0066150 A1 | 3/2015 | Dai et al. | |
| 2016/0157751 A1 * | 6/2016 | Mahfouz | A61B 5/062 600/409 |

FOREIGN PATENT DOCUMENTS

| | | |
|---|---|---|
| WO | WO-2015089118 A1 | 6/2015 |
| WO | WO-2017019382 A1 | 2/2017 |

OTHER PUBLICATIONS

"International Application Serial No. PCT/US2016/042943, Written Opinion dated Oct. 5, 2016", 9 pgs.

* cited by examiner

SYSTEM AND METHOD TO LOCATE SOFT TISSUE FOR PREOPERATIVE PLANNING

CLAIM OF PRIORITY

This application claims the benefit of U.S. Provisional Patent Application Ser. No. 62/196,496, filed on Jun. 24, 2015, the benefit of priority of which is claimed hereby, and which is incorporated by reference herein in its entirety.

BACKGROUND

In arthroplasty and some sports medicine surgeries, a damaged joint, such as a knee joint, is replaced with prosthetic implants. Prior to implantation of the implant, the damaged region of the joint is typically prepared by resecting or otherwise treating regions of the bones to provide surfaces that can align with and therefore accommodate the implant.

One of the predictors of an orthopedic arthroplasty outcome is appropriate selection and positioning of the prosthetic components. During orthopedic procedures, various tools and instruments are used to assist with prosthetic component selection and placement, including the use of templates as well as provisional or trial implant prosthetics. Such conventional tools and instruments may lack precision as they may rely on the user's judgment to assess proper positioning of the devices. In addition, each patient's anatomy being different, proper component sizing may be required for optimizing the outcome of the surgery. Still, conventional components may only allow patient customization to a certain degree.

Overview

Example systems and methods for determining a patient specific soft tissue location within a joint of a patient are described. Based at least in part on the patient-specific soft tissue location, the example systems and methods can also be utilized in preoperative planning, to aid in selection or create a surgical jig and/or to aid in selection of a prosthesis. According to some examples, the systems and methods can be used in preoperative planning to provide the user with instructions, visual aids, information, recommendations, automated measurements, and so on as to the location, size, and other properties of soft tissue, bone, and/or prostheses relevant to the procedure. In the following description, for purposes of explanation, numerous specific details are set forth in order to provide a thorough understanding of examples provided. It will be evident, however, to one skilled in the art that examples of the present invention may be practiced without these specific details or details may be modified to a degree. It will also be evident that the systems and methods discussed are not limited to the examples provided and may include other scenarios not specifically discussed. For example, the methodologies discussed herein with respect to a knee arthroscopy can be similarly applied to other procedures (e.g., reconstructing the PCL or other ligamentous structures for sports medicine surgery, a total hip or total shoulder replacement, among others).

Understanding the location of soft tissue structures is important in many orthopedic procedures. For example, soft tissue location can affect the size and shape of prosthetic implant installed, as well as the shape of a jig used to ensure accurate position and orientation of finishing instruments during bone resection of a knee arthroscopy. For example, understanding the location and shape of the anterior cruciate ligament (ACL) and/or posterior cruciate ligament (PCL) can be beneficial when placing both medial and lateral femoral and tibia implants in a unicompartmental knee arthroscopy, making a tibial cut and placing the tibial component in a cruciate retaining total knee arthroscopy, and making bone cuts and placing implants in a bi-cruciate sparing total knee arthroscopy.

Preoperative planning including templating can be performed in clinical practice to determine the size and shape of implants and jigs likely to best fit the anatomy of the individual. In order to further refine preoperative practice, the current inventors recognized that understanding the location of a patient's soft tissue can be instructive. Current planning technology does not seek such understanding as it can be expensive to gather, inaccurate, and time consuming. Accordingly, the inventors preformed cadaver and imaging studies on hundreds of knee joints to determine the size and location of soft tissue (e.g., ACL, PCL) relative to the morphology (e.g., size and/or features) of the tibia and femur. From such measurements, the inventors derived various databases, methodologies, and systems as disclosed herein. According to some examples provided herein, the disclosed databases, methodologies, and systems can be used to locate soft tissue for preoperative planning when used in combination with radiographic or similar medical images of a patient's joint.

To further illustrate the components and methods disclosed herein, a non-limiting list of examples is provided here:

In Example 1, a method can comprise imaging a target location for an orthopedic implant to collect image data regarding a morphology of the patient, the morphology including at least one of bone size and bone feature, accessing stored soft tissue data and bone data corresponding to the target location of the orthopedic implant, determining the location of a soft tissue of the patient based at least in part upon the soft tissue data and bone data and the image data, and displaying data including the location of the soft tissue of the patient.

In Example 2, the method of Example 1, can comprise constructing, based at least in part on the location of the soft tissue, a virtual model of the target location, wherein the virtual model displays a contour of the soft tissue.

In Example 3, the method of any one or any combination of Examples 1 or 2, can comprise recommending a prosthesis to best fit one or more of a femur and tibia of the patient.

In Example 4, the method of any one or any combination of Examples 1 to 3, can comprise fabricating a patient-specific jig for preparing an articular surface of a bone in the target location a design of the jig based at least in part upon the location of the soft tissue.

In Example 5, the method of any one or any combination of Examples 1 to 4, wherein the morphology can further include one of a soft tissue shape and soft tissue location.

In Example 6, the method of any one or any combination of Examples 1 to 5, wherein the soft tissue can comprise at least one of an ACL and a PCL and locating the soft tissue can comprise: creating an average of one or more of an ACL and PCL contour for one or more of an average femur and tibia from the soft tissue data and bone data corresponding to the target location of the orthopedic implant, altering one or more of the average femur and tibia to match one or more of a femur and tibia of the patient, and altering one or more of an ACL and PCL contour of the patient with the step of altering one or more of the average femur and tibia.

In Example 7, the method of any one or any combination of Examples 1 to 6, wherein imaging can comprise use of one or more of X-Ray, Fluoroscopy, Computerized Tomography, True size imaging, and MRI.

In Example 8, the method of any one or any combination of Examples 1 to 7, can comprise producing one or more of anatomical measurement, instruction, recommendation, information, and visual aid.

In Example 9, a system can comprise a computer including at least one processor and a memory device, the memory device including instructions that, when executed by the at least one processor, cause the computer to: access image data of a target location for an orthopedic implant, the image data including data regarding at least one of bone size and bone feature of the patient, access stored soft tissue data and bone data corresponding to the target location of the orthopedic implant, compare the image data to the soft tissue and bone data, and determine, based at least in part on the soft tissue data and bone data, a location of the soft tissue within the target location.

In Example 10, the system of Example 9, can further comprise instructions that cause the computer to construct a virtual model of the target location, wherein the virtual model includes a display of a contour of the soft tissue.

In Example 11, the system of any one or any combination of Examples 9 and 10, can further comprise instructions that cause the computer to recommend, based at least in part on the location of the soft tissue, a prosthesis to best fit one or more of a femur and tibia of the patient.

In Example 12, the system of any one or any combination of Examples 9 to 11, can further comprise instructions that cause the computer to provide instruction, based at least in part upon the location of the soft tissue, regarding a design of a patient-specific jig for preparing an articular surface of a bone in the target location.

In Example 13, the system of any one or any combination of Examples 9 to 12, wherein the image data can include soft tissue shape and soft tissue location.

In Example 14, the system of any one of Examples 9 to 13, wherein the soft tissue can comprise at least one of an ACL and a PCL and instructions that can cause the computer to determine the location of the soft tissue include instructions to cause the computer to: create an average of one or more of an ACL and PCL contour for one or more of an average femur and tibia from the soft tissue data and bone data corresponding to the target location of the orthopedic implant, alter one or more of the average femur and tibia to match one or more of a femur and tibia of the patient, and alter one or more of an ACL and PCL contour of the patient with the step of altering one or more of the average femur and tibia.

In Example 15, the system of any one of Examples 9 to 14, can further comprise instructions that cause the computer to perform one or more of providing at least one anatomical measurement, at least one instruction, at least one recommendation, provide at least one of information, and at least one visual aid.

In Example 16, a machine-readable storage device can include instructions that, when executed by a machine, cause the machine to: access image data of a target location for an orthopedic implant, the image data including data regarding at least one of bone size and bone feature of the patient, access stored soft tissue data and bone data corresponding to the target location of the orthopedic implant, compare the image data to the soft tissue and bone data, and determine, based at least in part on the soft tissue data and bone data, a location of the soft tissue within the target location.

In Example 17, the machine-readable storage device of Example 16, can further include instructions to cause the machine to construct a virtual model of the target location, wherein the virtual model includes a display of a contour of the soft tissue.

In Example 18, the machine-readable storage device of any one or any combination of Examples 16 and 17, can further include instructions to cause the machine to recommend, based at least in part on the location of the soft tissue, a prosthesis to best fit one or more of a femur and tibia of the patient.

In Example 19, the machine-readable storage device of any one or any combination of Examples 16 to 18, can further include instructions to cause the machine to provide instruction, based at least in part upon the location of the soft tissue, regarding a design of a patient-specific jig for preparing an articular surface of a bone in the target location.

In Example 20, the machine-readable storage device of any one or any combination of Examples 16 to 19, wherein the soft tissue can comprise at least one of an ACL and a PCL and instructions can cause the machine to determine the location of the soft tissue include instructions to cause the machine to: create an average of one or more of an ACL and PCL contour for one or more of an average femur and tibia from the soft tissue data and bone data corresponding to the target location of the orthopedic implant, alter one or more of the average femur and tibia to match one or more of a femur and tibia of the patient, and alter one or more of an ACL and PCL contour of the patient with the step of altering one or more of the average femur and tibia.

In Example 21, the system or method of any one or any combination of Examples 1-20 can optionally be configured such that all elements or options recited are available to use or select from.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1:
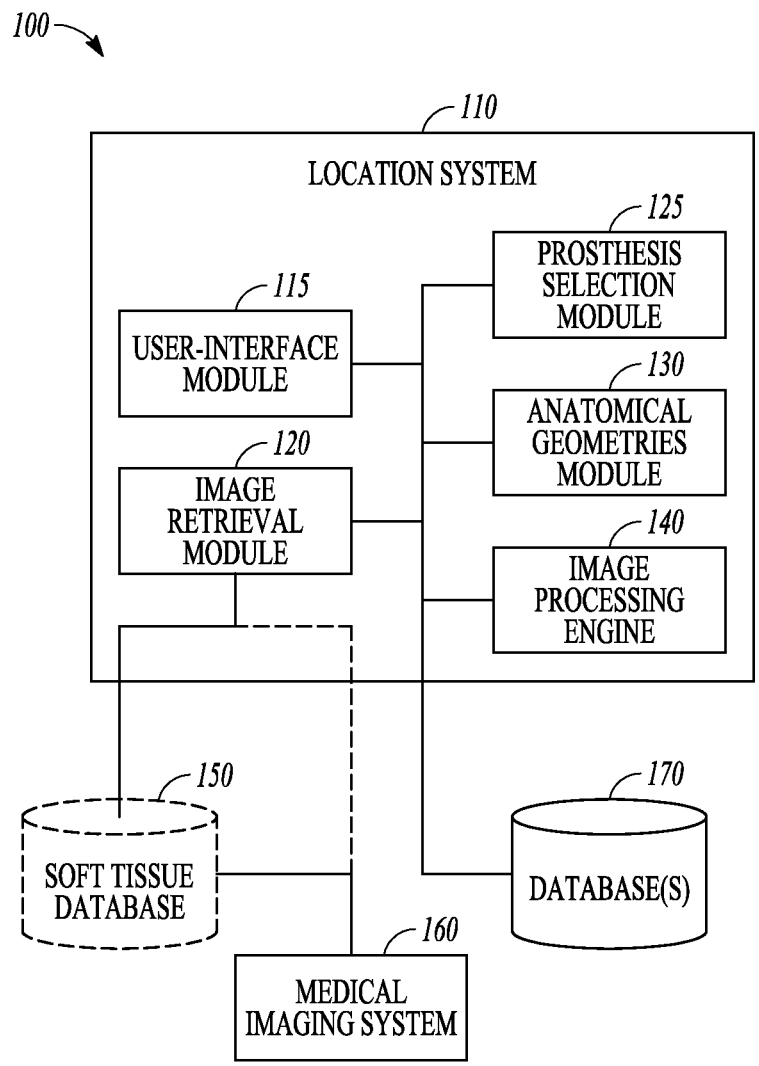
FIG. 1 is a block diagram illustrating a system for preoperative planning based on location of soft tissue, according to an example of the present disclosure.

Example systems and methods for determining a patient specific soft tissue location within a joint of a patient are described. Based at least in part on the patient specific soft tissue locations, the example systems and methods can also be utilized in preoperative planning, to aid in selection or creation of a surgical jig and/or to aid in selection of a prosthesis based on the patient specific soft tissue locations. In the example of FIG. 1, a physician or other personnel can use a system, such as system 100, to locate soft tissue in the applicable joint of a patient. The system 100 can also be utilized by the user to aid in selection of a prosthesis and/or aid in creation of a jig. Such selection or creation can be based upon the location and other characteristics of the soft tissue, for example. In FIG. 1, the system 100 can include a location system 110 receiving data from one or more of a soft tissue database 150, a medical imaging system 160, or one or more additional databases 170. In some examples, the location system 110 can include a user-interface module 115, an image retrieval module 120, a selection module 125, an anatomical geometries module 130, and an image processing engine 140.

In an example, the user-interface module 115 can receive input from a user and provide feedback on the resulting measurements, soft tissue locations, calculations, and resection locations, for example. According to some examples, the user-interface module 115 can provide guidance for jig and/or prosthesis selection in view of the soft tissue size, location, bone morphology, etc. In one example, the user-interface module 115 can process inputs such as the selection of joint morphology (e.g., bone size, bone features, soft tissue location) on a medical image of a region of interest within the medial image of the joint. Additionally, the user-interface module 115 can process inputs and provide output associated with other aspects of the location system 110. According to some examples, the user-interface module 115 can interface with user-interface components, such as a display and user-input mechanism (e.g., mouse, keyboard, or touch screen).

In an example, the image retrieval module 120 can retrieve a medical image for processing by the location system 110 from sources, such as the soft tissue database 150 or the medical imaging system 160, among others. The image retrieval module 120 can communicate directly with the medical imaging system 160 to receive a radiographic (or similar) medical image of a patient's joint for processing by the location system 110. Medical image processed by the location system 110 can be of any type of medical image that depicts internal structures of a patient's joint and soft tissue. Technologies such as X-Ray, Fluoroscopy, Computerized Tomography (CT), True size imaging (EOS™), and MRI can all produce usable images. Other imaging technologies can be used with the methods and systems discussed herein.

The image processing engine 140 can run various imagine processing algorithms on the medical images retrieved by the image retrieval module 120. The image processing engine 140 can use image processing algorithms such as thresholding, edge detection, contrast detection, contrast-edge detection, and other known image processing techniques to perform the automated measurements discussed in more detail below.

According to the example of FIG. 1, the anatomical geometries module 130 can use data generated by the image processing engine 140 and/or the location system 110 to perform calculations to describe or characterize the geometry of one or more bones of the joint. These calculations can determine, for example, anterior/posterior and/or medial/lateral bone dimensions, bone axes/landmarks/positions, relative positions between bones, curvature and surface topography of the bone or articular surface, and/or soft tissue attachment size and/or location, and the like. Bone landmarks can include the size, shape, position of the medial and lateral condyle, medial and lateral epicondyle, tibial tuberosity, trochlear groove, intercondylar notch, PCL facet, tibial eminence, and/or tibular head, for example. According to some examples, the selection module 125 can use the calculations generated by the anatomical geometries module 130 and the location system 110 to select an appropriate patient specific prosthetic implant and/or to prototype or select a patient specific jig. For example, the prosthesis selection module 125 can utilize the soft tissue location data as supplied by the location system 110 and the dimensions of the available prosthetic implants to optimize fit. Such calculation can be based on the location of the soft tissue relative to the measured geometries of the patient's distal femur and/or proximal tibia in the case of a knee arthroplasty, for example. According to some examples, the prosthesis selection module 125 can look up prosthetic implant sizing information from the database 170.

According to one example, a method is disclosed that utilizes imaging data from a patient and performs calculations from the imaging data including determining locations of relevant soft tissue structures. From the calculations, surgical decisions including the size of implants and the placement of the implant on the patient can be determined. The surgical decisions can be visualized electronically prior to being implemented. Based upon the visualization, the surgeon can alter his or her decision as desired.

Figure 2:
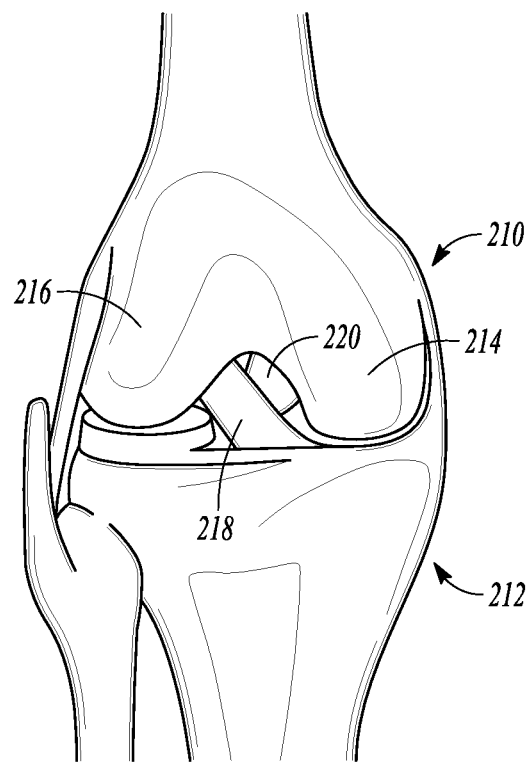
FIG. 2 is an anterior view of a natural femur and tibia.
Figure 2A:
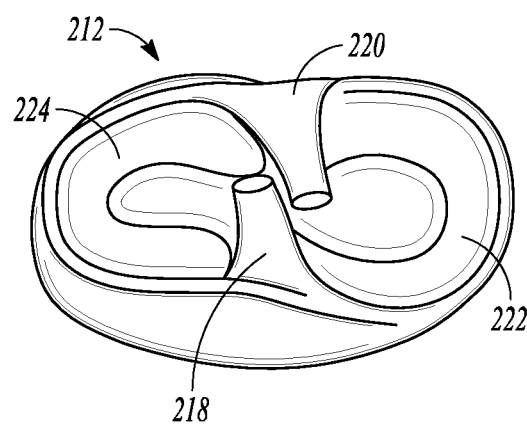
FIG. 2A is an elevated view of the tibia of FIG. 2.

FIG. 2 illustrates a natural femur 210 and tibia 212. The femur 210 can include medial 214 and lateral 216 condyles at a distal end of the femur 210. Various soft tissues (e.g., ligaments) can be attached to the femur 210 and/or the tibia 212. For example, the anterior cruciate ligament (ACL) 218 can extend from an anterior side of the tibia 212 to the femur 210, and the posterior cruciate ligament (PCL) 220 can extend from a posterior side of the tibia 212 to the femur 210. FIG. 2A is a top view of the tibia 212 and further illustrates some of these soft tissues as well as a medial meniscus 222 and a lateral meniscus 224 that are located between the tibia 212 and the medial 214 and lateral 216 condyles.

Figure 3:
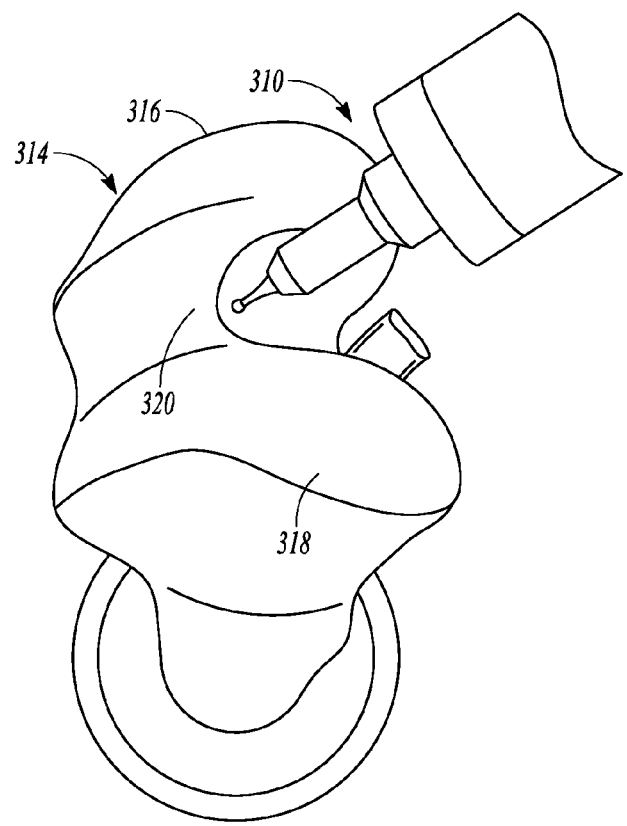
FIG. 3 is a perspective view of a tool positioned adjacent a distal end of the femur and adapted to measure the location of the soft tissues, according to an example of the present disclosure.

FIG. 3 illustrates a sensor 310 that can be adapted to sense the morphology (e.g., bone size, bone features, soft tissue shape and location) in a patient's joint 312. The sensor 310 can be part of a portable coordinate measurement machine (CMM). It is used to measure the three dimensional location of a point with respect to the base of the machine. It can be used to map the surface of a bone and also the location of soft tissue structures on that bone. The information gathered by the sensor 310 can be used in the soft tissue database 150 and/or databases 170 as described in FIG. 1. In the example of FIG. 3, the sensor 310 is illustrated measuring a size and other geometry of a distal femur 314. According to some examples, the sensor 310 can be used to measure a location of where the ACL and PCL connect to the distal femur 314. The size and geometry of features of the distal femur (e.g., medial femoral condyle 316, lateral femoral condyle 318, patellar sulcus 320, and the size and geometry of features of the proximal tibia (e.g. medial and lateral plateau, medial and lateral eminence peaks, tubercle, lateral and medial epicondyle, popliteal sulcus, and so on) can also be measured and located using the sensor 310 and that data, along with the associated soft tissue location data can be stored for access. As will be discussed subsequently, the data can be used to generate algorithms that are adapted to predict a location and/or shape of a patient's soft tissue based upon medical images of the patient's joint taken preoperatively. According to some examples, data regarding bone size and bone features can be cross-referenced to associated soft tissue size, location, and shape. Algorithms can be generated that can utilize bone size and/or bone features as ascertained by medical images to aid in the prediction of associated soft tissue size, location, and shape.

Figure 4:
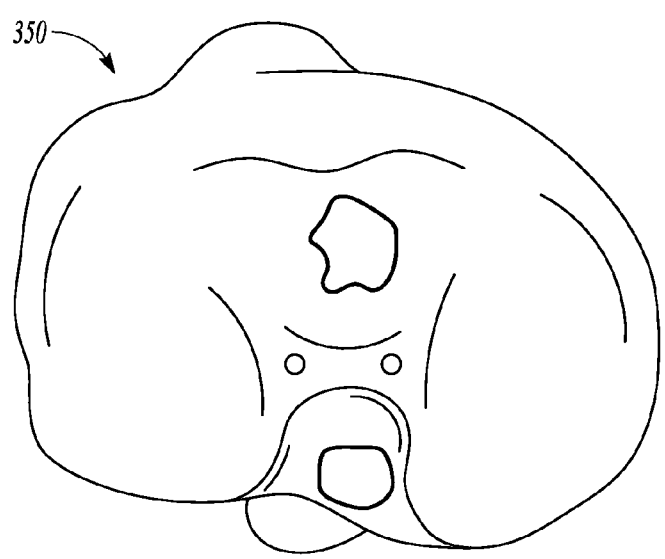
FIG. 4 is an image of the proximal end of a tibia overlaid with data as collected by the tool of FIG. 4, according to an example of the present disclosure.

FIG. 4 shows an image of a proximal portion of a tibia 350. According to FIG. 4, the image can be generated from image data collected using imaging technology and can be overlaid with data collected during various tests using the sensor 310 (FIG. 3). As shown in FIG. 4, the collected data can include a location of the ACL and PCL on the proximal tibia and can include a location of the lateral and medial intercondyle eminences.

Figure 5:
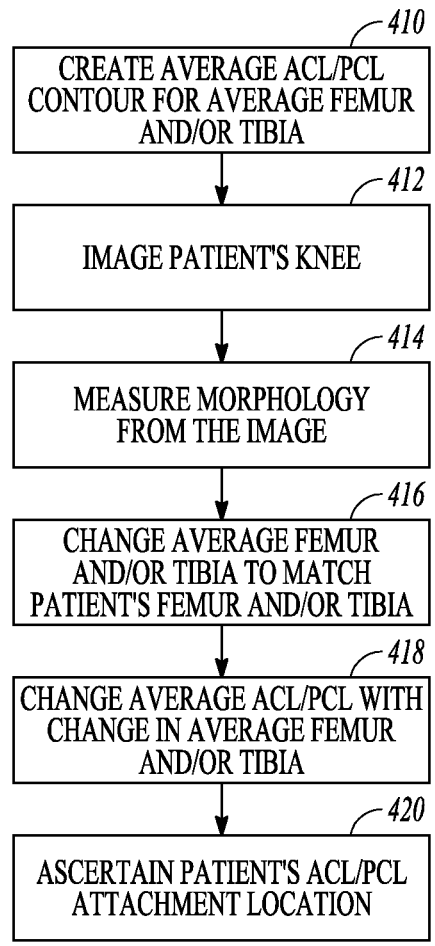
FIG. 5 is a flowchart illustrating a method for determining a patient specific soft tissue location, according to an example of the present disclosure.

FIG. 5 is a flowchart illustrating a method for determining a patient specific soft tissue location according to an example of the present disclosure. The method can create 410 an average ACL and/or PCL contour for an average femur and/or tibia. The contour can include one or more of attachment location, size, and shape of the ACL and/or PCL. The creation of the average ACL and/or PCL contour can be derived from the database of femoral and tibial data with identified (known) ACL and/or PCL attachment location information as discussed previously. The method can image 412 the patient's knee and measure 414 the morphology of one or more of the bones (including size, shape, curvature, bone features, etc.) from the image. The data can be derived from medical images using the imaging technologies as described previously. According to the example of FIG. 5, the method changes 416 (e.g., fits) the appropriate femur and/or tibia model in the database of step 410 to match that of the patient's femur and/or tibia. According to some examples, different models can be utilized for different sizes, genders, ethnicities, and so on. For example, this step can change the bone size and/or bone features of the selected knee model in the database to match the bone size and/or bone features of the patient's knee. In some examples, the method can morph geometry as desired, for example by performing a linear transformation. An example of such transformation can include, breaking the object (e.g., bone) into several two dimensional images, taking one of the two dimensional images and comparing it to another of the two dimensional images from the database, making both the images have the same number of points, moving the points in the second two dimensional image from the database to be equal to that of the initial two dimensional image from the patient, performing the prior activity with several of the two dimensional images, creating a mathematical transformation that describes the differences between the two shapes in three dimensions, and transforming any other information (e.g., bony information, soft tissue attachment site) from the database to the specific patient image(s).

Thus, the method can change 418 the PCL and/or ACL contour with the change in the average femur and/or tibia of step 416. According to the illustrated method, the attachment location (and/or other ACL and/or PCL information) can be ascertained 420 and such information can be utilized by the user for preoperative planning.

Figure 6:
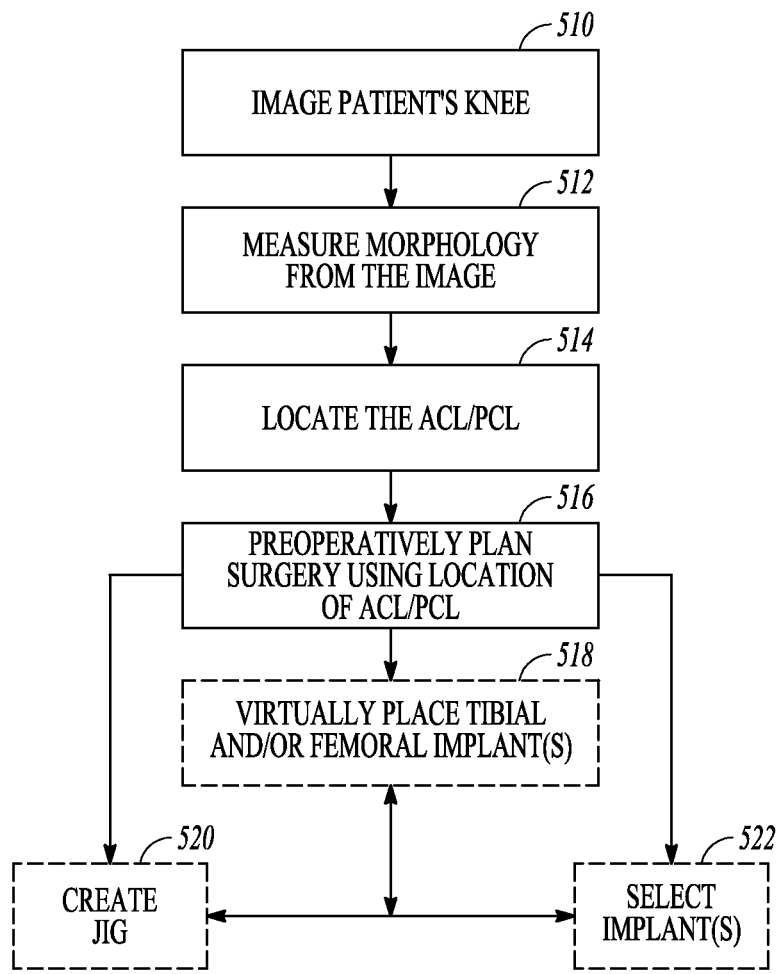
FIG. 6 is a flowchart illustrating a method for among other things selecting a prosthesis and/or jig based on the soft tissue location and other morphology, according to an example of the present disclosure.

FIG. 6 is a flowchart of a method for among other things preoperative planning, selecting a prosthesis, and/or selecting or fabricating a jig based on the soft tissue location and other patient morphology, according to an example of the present disclosure. The jig can be for arthroplasty or for perform ACL and PCL reconstruction as desired. According to the method of FIG. 6, the patient's knee can be imaged 510 and the morphology of the knee can be measured 512 as previously described. The ACL and/or PCL of the patient can be located 514 relative to the tibia and/or femur. The surgeon can preoperatively plan the patient's surgery 516 using the location of the ACL and/or PCL and other patient morphology (e.g., bone size, bone features). According to one example, preoperative planning can include providing instructions, visual aid, information, recommendation, and automated measurement to the surgeon. An example of preoperative planning software having such functionality is illustrated and further discussed in reference to FIG. 9. Examples of software, modules, and techniques that can be utilized with those disclosed herein are disclosed in United States Patent Application Publication 2015/0066150 A1 owned by the Applicant, and incorporated herein by reference in its entirety.

Figure 7:
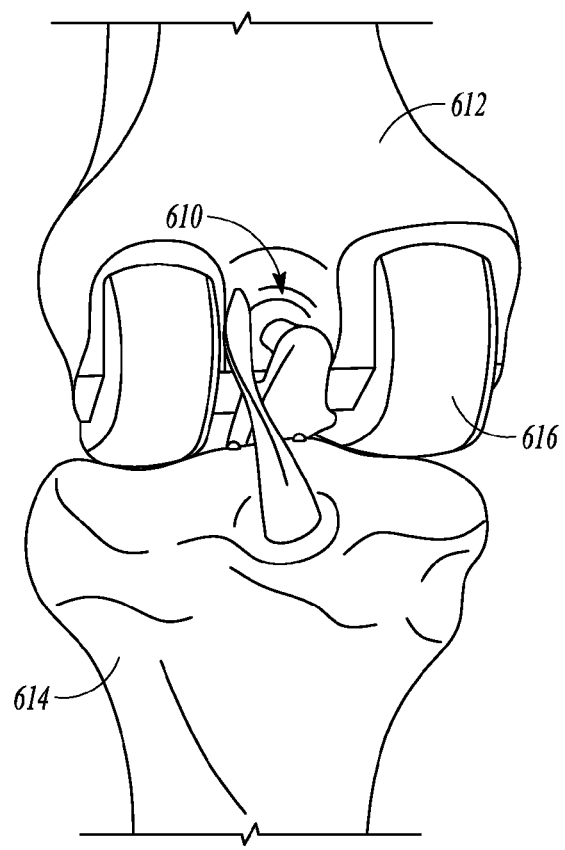
FIG. 7 is a virtual representation of the location of the soft tissues of a patient relative to the tibia, femur, and a prosthesis, according to an example of the present disclosure.
Figure 8:
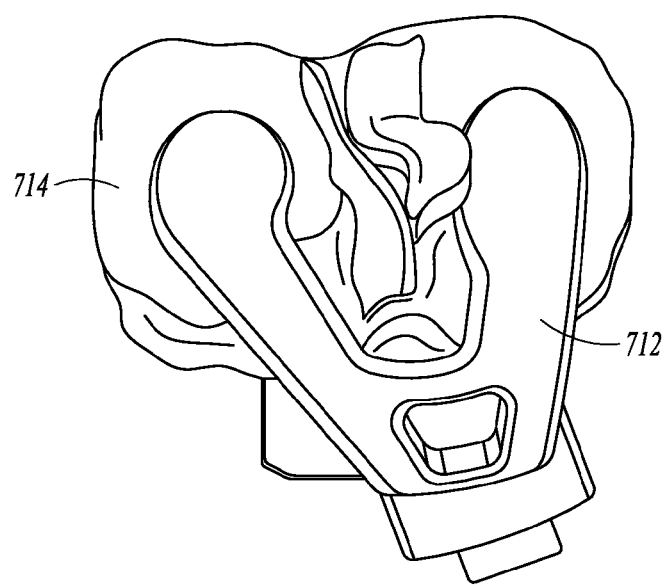
FIG. 8 is a view of the soft tissues, the femur and a surgical jig that can be created using information on the geometry of the patient's knee according to an example of the present disclosure.
Figure 9:
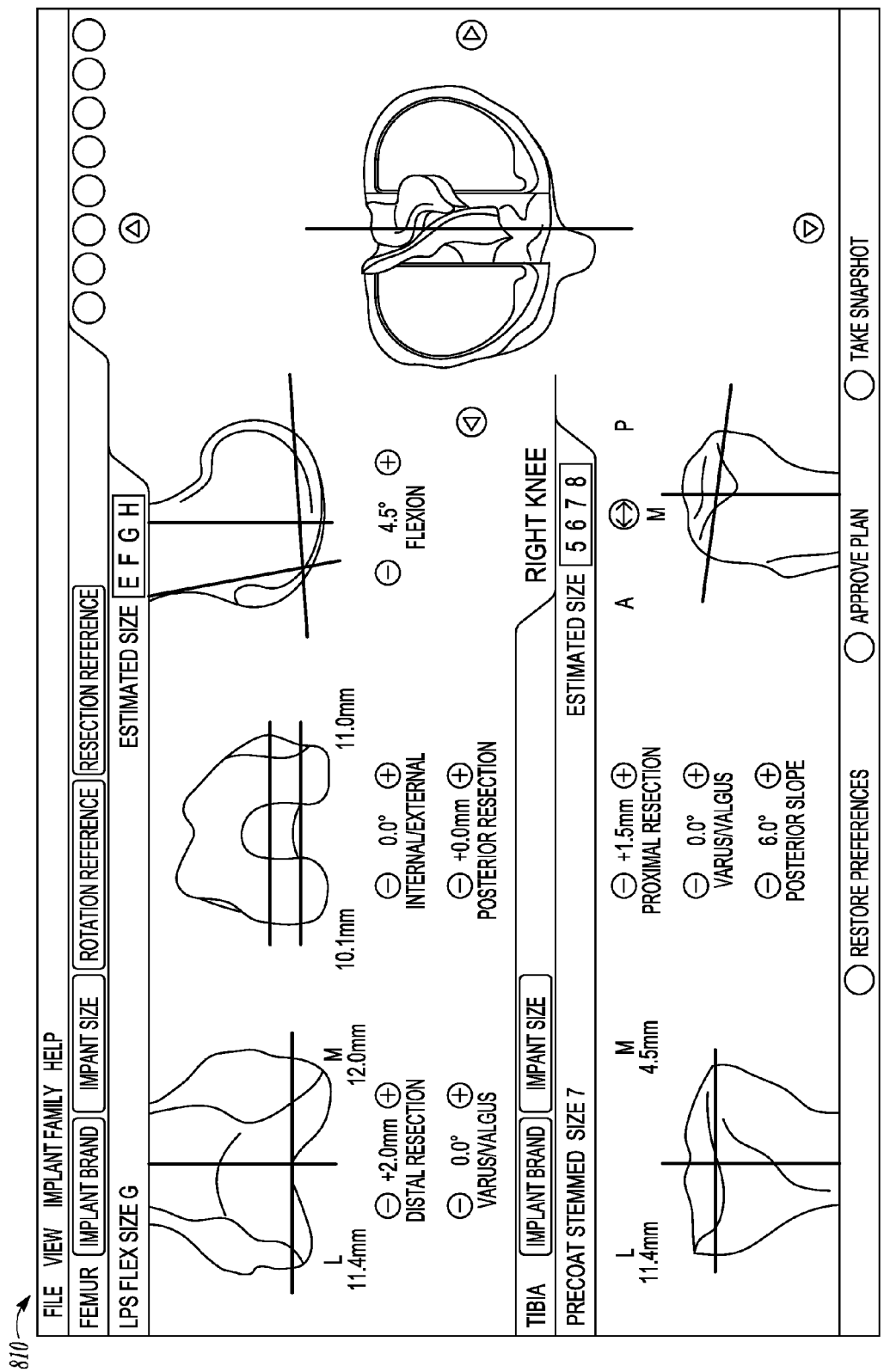
FIG. 9 is a screen shot image from a preoperative planning tool having a visual display with functionality according to systems and methods disclosed herein, according to an example of the present disclosure.

According to another example, the preoperative planning can visually display the location of the ACL and/or PCL as illustrated in FIGS. 7 and 9 and can allow the surgeon to virtually place tibial and/or femoral implants. According to further examples, the preoperative planning can visually display the location of the ACL and/or PCL for femoral jig sizing and placement as illustrated in FIG. 8. According to further examples, the method can create 520 or select a jig used to ensure accurate position and orientation of finishing instruments during bone resection as shown in FIG. 8. Examples of creation of a jig are described in U.S. Pat. No. 8,884,618 and United States Patent Application Publication 2013/0317510 A1 owned by the Applicant, and incorporated herein by reference in their entirety. In FIG. 6, the method can allow the user to select 522 appropriate tibial and/or femoral implants based upon the location of the ACL and/or PCL and other patient morphology (e.g., bone size, bone features). As illustrated in FIG. 6, virtual placement of the tibial and/or femoral implants, virtual display of the ACL and/or PCL, selection of implant(s), and creation of the jig can be interrelated or can be performed independent or semi-independent of one another.

FIG. 7 uses a virtual representations of the location of a patient's soft tissues 610 relative to a tibia 612, a femur 614, and a prosthesis 616, according to an example of the present disclosure. Such virtual representations can aid the surgeon in preoperative planning. For example, the surgeon can alter the size or brand of the implant and see the effects on the arthroplasty including any effects on the soft tissues 610. According to another example, the surgeon can change other aspects such as the location of one or more resections utilized for the knee arthroplasty and see the effects on the arthroplasty including any effects on the soft tissues 610. FIG. 8 uses a virtual representations of the location of a patient's soft tissues 710 for sizing and locating a jig 712 on a femur 714, according to an example of the present disclosure. Such virtual representations can aid the surgeon in preoperative planning.

FIG. 9 is a screen shot image of a preoperative planning tool 910 including a visual display generated for a surgeon for preoperative planning, according to an example of the present disclosure. As discussed, the planning tool 910 can include various functions such as providing instructions, visual aid, information, recommendation, and automated measurement to the surgeon.

In the example of FIG. 9, the planning tool 910 can allow the surgeon to visualize and alter resections (indicated by yellow lines) and can allow the surgeon to virtually install the implant(s) for review. The planning tool 910 can estimate a size of a femoral implant and tibial implant and display such size to the surgeon. The planning too 910 can also allow for the virtual selection and display of various implants according to size and/or brand. Furthermore, the planning tool 910 can virtually display the soft tissues of the patient according to the estimated location or actual as discussed herein.

Certain examples are described herein as including logic or a number of components, modules, or mechanisms. Modules may constitute either software modules (e.g., code embodied on a machine-readable medium or in a transmission signal) or modules. A module is tangible unit capable of performing certain operations and may be configured or arranged in a certain manner. In examples, one or more computer systems (e.g., a standalone, client or server computer system) or one or more modules of a computer system (e.g., a processor or a group of processors) may be configured by software (e.g., an application or application portion) as a module that operates to perform certain operations as described herein.

In various examples, a module may be implemented mechanically or electronically. For example, a module may comprise dedicated circuitry or logic that is permanently configured (e.g., as a special-purpose processor, such as a field programmable gate array (FPGA) or an application-specific integrated circuit (ASIC)) to perform certain operations. A module may also comprise programmable logic or circuitry (e.g., as encompassed within a general-purpose processor or other programmable processor) that is temporarily configured by software to perform certain operations. It will be appreciated that the decision to implement a module mechanically, in dedicated and permanently configured circuitry, or in temporarily configured circuitry (e.g., configured by software) may be driven by cost and time considerations.

Accordingly, the term "module" can be understood to encompass a tangible entity, such as hardware, that can be that an entity that is physically constructed, permanently configured (e.g., hardwired) or temporarily configured (e.g., programmed) to operate in a certain manner and/or to perform certain operations described herein. Considering examples in which modules are temporarily configured (e.g., programmed), each of the modules need not be configured or instantiated at any one instance in time. For example, where the modules comprise a general-purpose processor configured using software, the general-purpose processor may be configured as respective different modules at different times. Software may accordingly configure a processor, for example, to constitute a particular module at one instance of time and to constitute a different module at a different instance of time.

Modules can provide information to, and receive information from, other modules. Accordingly, the described modules may be regarded as being communicatively coupled. Where multiple of such modules exist contemporaneously, communications may be achieved through signal transmission (e.g., over appropriate circuits and buses) that connect the modules. In examples in which multiple modules are configured or instantiated at different times, communications between such modules may be achieved, for example, through the storage and retrieval of information in memory structures to which the multiple modules have access. For example, one module may perform an operation, and store the output of that operation in a memory device to which it is communicatively coupled. A further module may then, at a later time, access the memory device to retrieve and process the stored output. Modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some examples, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example examples, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Examples may be implemented in digital electronic circuitry, or in computer hardware, firmware, software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method operations can also be performed by, and apparatus of examples may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A method comprising:
   imaging a target location for an orthopedic implant to collect image data regarding a morphology of the patient, the morphology including at least one of bone size and bone feature;
   accessing stored soft tissue data and bone data corresponding to the target location of the orthopedic implant;
   determining the location of a soft tissue of the patient based at least in part upon the soft tissue data and bone data and the image data;
   displaying data including the location of the soft tissue of the patient; and
   recommending a prosthesis for selection from a database of prostheses to best fit the target location of the patient based at least in part upon the determined location of the soft tissue of the patient as well as at least one of the bone size and the bone feature, wherein the database of prostheses comprises information on implants of various brands and predetermined sizes.

2. The method of claim 1, comprising constructing, based at least in part on the location of the soft tissue, a virtual model of the target location, wherein the virtual model displays a contour of the soft tissue.

3. The method of claim 1, comprising fabricating a patient-specific jig for preparing an articular surface of a bone in the target location a design of the jig based at least in part upon the location of the soft tissue.

4. The method of claim 1, wherein the morphology further includes one of a soft tissue shape and soft tissue location.

5. The method of claim 1, wherein the soft tissue comprises at least one of an ACL and a PCL and locating the soft tissue comprises:
   creating an average of one or more of an ACL and PCL contour for one or more of an average femur and tibia from the soft tissue data and bone data corresponding to the target location of the orthopedic implant;
   altering one or more of the average femur and tibia to match one or more of a femur and tibia of the patient; and
   altering one or more of an ACL and PCL contour of the patient with the step of altering one or more of the average femur and tibia.

6. The method of claim 1, wherein imaging comprise use of one or more of X-Ray, Fluoroscopy, Computerized Tomography, True size imaging, and MRI.

7. The method of claim 1, comprising producing one or more of anatomical measurement, instruction, recommendation, information, and visual aid.

8. A system comprising:
   a computer including at least one processor and a memory device, the memory device including instructions that, when executed by the at least one processor, cause the computer to:

access image data of a target location for an orthopedic implant, the image data including data regarding at least one of bone size and bone feature of the patient;
access stored soft tissue data and bone data corresponding to the target location of the orthopedic implant;
compare the image data to the soft tissue and bone data;
determine, based at least in part on the soft tissue data and bone data, a location of the soft tissue within the target location;
recommend, based at least in part on the location of the soft tissue within the target location, a prosthesis for selection from a database of prostheses to best fit the target location, wherein the database of prostheses comprises information on implants of various brands and predetermined sizes;
construct a virtual model of the target location, wherein the virtual model includes a display of a contour of the soft tissue; and
display the selected prosthesis superimposed on the virtual model with the display of the contour of the soft tissue.

9. The system of claim 8, further comprising instructions that cause the computer to provide instruction, based at least in part upon the location of the soft tissue, regarding a design of a patient-specific jig for preparing an articular surface of a bone in the target location.

10. The system of claim 8, wherein the image data includes soft tissue shape and soft tissue location.

11. The system of claim 8, wherein the soft tissue comprises at least one of an ACL and a PCL and instructions that cause the computer to determine the location of the soft tissue include instructions to cause the computer to:
create an average of one or more of an ACL and PCL contour for one or more of an average femur and tibia from the soft tissue data and bone data corresponding to the target location of the orthopedic implant;
alter one or more of the average femur and tibia to match one or more of a femur and tibia of the patient; and
alter one or more of an ACL and PCL contour of the patient with the step of altering one or more of the average femur and tibia.

12. The system of claim 8, further comprising instructions that cause the computer to perform one or more of providing at least one anatomical measurement, at least one instruction, at least one recommendation, provide at least one of information, and at least one visual aid.

13. A machine-readable storage device including instructions that, when executed by a machine, cause the machine to:
access image data of a target location for an orthopedic implant, the image data including data regarding at least one of bone size and bone feature of the patient;
access stored soft tissue data and bone data corresponding to the target location of the orthopedic implant;
compare the image data to the soft tissue and bone data;
determine, based at least in part on the soft tissue data and bone data, a location of the soft tissue within the target location; and
recommend, based at least in part on the location of the soft tissue within the target location, a prosthesis for selection from a database of prostheses to best fit the target location;
wherein the soft tissue comprises at least one of an ACL and a PCL and the instructions cause the machine to determine the location of the soft tissue include instructions to cause the machine to:
create an average of one or more of an ACL and PCL contour for one or more of an average femur and tibia from the soft tissue data and bone data corresponding to the target location of the orthopedic implant;
alter one or more of the average femur and tibia to match one or more of a femur and tibia of the patient; and
alter one or more of an ACL and PCL contour of the patient with the step of altering one or more of the average femur and tibia.

14. The machine-readable storage device of claim 13, further including instructions to cause the machine to construct a virtual model of the target location, wherein the virtual model includes a display of a contour of the soft tissue.

15. The machine-readable storage device of claim 13, further including instructions to cause the machine to provide instruction, based at least in part upon the location of the soft tissue, regarding a design of a patient-specific jig for preparing an articular surface of a bone in the target location.

* * * * *